United States Patent [19]
Li

[11] Patent Number: 5,741,300
[45] Date of Patent: Apr. 21, 1998

[54] SURGICAL ANCHOR AND PACKAGE AND CARTRIDGE FOR SURGICAL ANCHOR

[75] Inventor: Lehmann K. Li, Milford, Conn.

[73] Assignee: Li Medical Technologies, Inc., Shelton, Conn.

[21] Appl. No.: 711,988

[22] Filed: Sep. 10, 1996

[51] Int. Cl.⁶ .................................................. A61B 17/04
[52] U.S. Cl. .......................... 606/232; 206/339; 206/341
[58] Field of Search ........................... 606/232, 151, 606/142, 143; 206/338–341

[56] References Cited

U.S. PATENT DOCUMENTS

| | | |
|---|---|---|
| Re. 34,293 | 6/1993 | Goble et al. . |
| Re. 34,762 | 10/1994 | Goble et al. . |
| 1,247,621 | 11/1917 | Bennett . |
| 2,100,570 | 11/1937 | Saleh . |
| 2,143,086 | 1/1939 | Pleister . |
| 2,213,715 | 9/1940 | Monahan . |
| 2,453,056 | 11/1948 | Zack . |
| 2,562,419 | 4/1951 | Ferris . |
| 3,048,177 | 8/1962 | Takaro . |
| 3,155,095 | 11/1964 | Brown . |
| 3,254,650 | 6/1966 | Collito . |
| 4,011,602 | 3/1977 | Rybicki et al. . |
| 4,233,981 | 11/1980 | Schomacher . |
| 4,293,259 | 10/1981 | Liebig . |
| 4,447,915 | 5/1984 | Webr . |
| 4,454,612 | 6/1984 | McDaniel et al. . |
| 4,501,266 | 2/1985 | McDaniel . |
| 4,708,132 | 11/1987 | Silvestrini . |
| 4,738,255 | 4/1988 | Goble et al. . |
| 4,741,330 | 5/1988 | Hayhurst . |
| 4,744,793 | 5/1988 | Pavr et al. . |
| 4,747,407 | 5/1988 | Liu et al. . |
| 4,759,765 | 7/1988 | Van Kampen . |
| 4,772,286 | 9/1988 | Goble et al. . |
| 4,776,330 | 10/1988 | Chapman et al. . |
| 4,870,957 | 10/1989 | Goble et al. . |
| 4,875,474 | 10/1989 | Border . |
| 4,892,547 | 1/1990 | Brown . |
| 4,898,156 | 2/1990 | Gatturna . |
| 4,899,743 | 2/1990 | Nicholson et al. . |
| 4,901,711 | 2/1990 | Goble et al. . |
| 4,911,153 | 3/1990 | Border . |
| 4,927,421 | 5/1990 | Goble et al. ...................... 606/232 |
| 4,946,468 | 8/1990 | Li . |
| 4,959,071 | 9/1990 | Brown et al. . |
| 4,960,420 | 10/1990 | Goble et al. . |
| 4,968,315 | 11/1990 | Gatturna . |
| 4,985,032 | 1/1991 | Goble ............................ 606/232 |
| 4,986,263 | 1/1991 | Dickerson et al. . |
| 4,997,433 | 3/1991 | Goble et al. .................... 606/232 |
| 5,002,550 | 3/1991 | Li . |
| 5,002,574 | 3/1991 | May et al. . |
| 5,011,473 | 4/1991 | Gatturna . |
| 5,013,316 | 5/1991 | Goble et al. . |
| 5,019,105 | 5/1991 | Wiley . |
| 5,037,422 | 8/1991 | Hayhurst . |
| 5,037,426 | 8/1991 | Goble et al. . |
| 5,046,513 | 9/1991 | Gatturna . |
| 5,078,730 | 1/1992 | Li . |
| 5,084,058 | 1/1992 | Li . |

(List continued on next page.)

FOREIGN PATENT DOCUMENTS

| | | |
|---|---|---|
| 0270704 | 6/1988 | European Pat. Off. . |
| 1368021 | 6/1964 | France . |
| 2622430 | 5/1989 | France . |
| 0343992 | 3/1931 | United Kingdom . |
| 9204874 | 4/1992 | WIPO . |

*Primary Examiner*—Gary Jackson
*Attorney, Agent, or Firm*—Ostrolenk, Faber, Gerb & Soffen, LLP

[57] ABSTRACT

A cartridge for holding a generally cylindrical surgical fastener in position for ease of handling, comprising a holder having a surface for grasping by a user, the holder having a cup-shaped surface for engagement with the surgical fastener and for fixing the fastener in position on the holder and a threading loop extending from the holder for extending through an aperture in the surgical fastener. A combination, preferably provided as a sterile packaged unit includes the cartridge and the surgical fastener and may also include the suture and a surgical fastener emplacement tool.

39 Claims, 8 Drawing Sheets

U.S. PATENT DOCUMENTS

| | | | |
|---|---|---|---|
| 5,087,263 | 2/1992 | Li . | |
| 5,092,891 | 3/1992 | Kummer et al. . | |
| 5,094,563 | 3/1992 | Carletti . | |
| 5,129,902 | 7/1992 | Goble et al. . | |
| 5,133,723 | 7/1992 | Li et al. . | |
| 5,141,520 | 8/1992 | Goble et al. . | |
| 5,147,362 | 9/1992 | Goble . | |
| 5,152,764 | 10/1992 | Goble . | |
| 5,161,916 | 11/1992 | White et al. . | |
| 5,163,946 | 11/1992 | Li . | |
| 5,174,087 | 12/1992 | Bruno . | |
| 5,176,682 | 1/1993 | Chow . | |
| 5,192,303 | 3/1993 | Gatturna et al. . | |
| 5,203,787 | 4/1993 | Noblitt et al. . | |
| 5,207,679 | 5/1993 | Li . | |
| 5,217,486 | 6/1993 | Rice et al. . | |
| 5,250,058 | 10/1993 | Miller et al. . | |
| 5,263,991 | 11/1993 | Wiley et al. . | |
| 5,266,075 | 11/1993 | Clark et al. . | |
| 5,268,001 | 12/1993 | Nicholson et al. . | |
| 5,300,077 | 4/1994 | Howell . | |
| 5,306,290 | 4/1994 | Martins et al. . | |
| 5,312,416 | 5/1994 | Spaeth et al. . | |
| 5,312,422 | 5/1994 | Trott . | |
| 5,312,438 | 5/1994 | Johnson . | |
| 5,313,962 | 5/1994 | Obenchain . | |
| 5,314,427 | 5/1994 | Goble et al. | 606/232 |
| 5,314,429 | 5/1994 | Goble | 606/232 |
| 5,314,433 | 5/1994 | Li . | |
| 5,318,577 | 6/1994 | Li | 606/232 |
| 5,324,308 | 6/1994 | Pierce | 606/232 |
| 5,330,534 | 7/1994 | Herrington et al. . | |
| 5,342,366 | 8/1994 | Whiteside et al. . | |
| 5,350,380 | 9/1994 | Goble et al. . | |
| 5,354,298 | 10/1994 | Lee et al. . | |
| 5,354,300 | 10/1994 | Goble et al. . | |
| 5,356,413 | 10/1994 | Martins et al. . | |
| 5,358,511 | 10/1994 | Gatturna et al. . | |
| 5,372,599 | 12/1994 | Martins . | |
| 5,372,604 | 12/1994 | Trott . | |
| 5,376,120 | 12/1994 | Sarver et al. . | |
| 5,393,302 | 2/1995 | Clark et al. . | |
| 5,443,482 | 8/1995 | Stone et al. . | |
| 5,464,425 | 11/1995 | Skiba . | |
| 5,464,427 | 11/1995 | Curtis et al. . | |
| 5,486,197 | 1/1996 | Le et al. . | |
| 5,531,792 | 7/1996 | Huene . | |
| 5,534,004 | 7/1996 | Santangelo . | |
| 5,545,180 | 8/1996 | Le et al. . | |

SURGICAL ANCHOR AND PACKAGE AND CARTRIDGE FOR SURGICAL ANCHOR

BACKGROUND OF THE INVENTION

The present invention relates to surgical fasteners and in particular, to surgical anchors suitable for fastening sutures in bio-organic materials, for example, bone. More particularly, the present invention relates to a cartridge for holding a surgical fastener or anchor for ease of handling prior to insertion. The invention also relates to a combination comprising a cartridge and a surgical fastener, preferably disposed in a sterile package. The invention also relates to the surgical anchor itself.

This application is related to co-pending U.S. application Ser. No. 08/426,715 (2346-7), commonly owned by the Assignee of the present application. U.S. application Ser. No. 08/426,715 discloses a surgical bone anchor or fastener for fastening sutures to bone. That application discloses various embodiments of bone anchors including a bone anchor of the type shown in this application. The present application relates to a convenient cartridge assembly for holding the suture anchor, for threading a suture into the suture anchor and for holding the suture anchor in a convenient position prior to its engagement and fixation by a suture anchor emplacement device. The present application also relates to an improvement to the surgical anchor disclosed in the above-described co-pending application.

Reference is also made to commonly assigned copending U.S. application Ser. No. 08/294,067 (2346-2) for a basic disclosure of surgical anchors of the type described herein.

SUMMARY OF THE INVENTION

It is an object of the present invention to provide a cartridge and holder for a suture anchor of the type disclosed in the above co-pending application.

Still a further object of the present invention is to provide a convenient means for threading a suture onto a suture anchor of the type disclosed in the above co-pending application.

Yet still a further object of the present invention is to provide a device comprising a combination of a cartridge for holding a suture anchor and a suture anchor.

It is yet still a further object of the present invention to provide an improvement to the surgical anchors disclosed in the above described co-pending patent applications.

The above and other objects of the present invention are achieved by a cartridge for holding a surgical fastener in position for ease of handling, comprising, a holder having a surface for grasping by a user, the holder having a concave surface for engagement with the surgical fastener and for fixing the fastener in position on the holder, and a threading loop extending from the holder for extending through an aperture in the surgical fastener.

The objects of the invention are also achieved by a combination comprising, a cartridge for holding a surgical fastener in position for ease of handling, the cartridge comprising a holder having a surface for grasping by a user, the holder having a surface for engagement with the surgical fastener and for fixing the fastener in position on the holder, a threading loop extending from the holder for extending through an aperture in the surgical fastener, and a surgical fastener engaged by said holder with the threading loop disposed through the aperture in the surgical fastener.

The objects of the invention are furthermore achieved by a combination comprising a cartridge for holding a surgical fastener in position for ease of handling, the cartridge comprising, a holder having a surface for grasping by a user, the holder having a surface for engagement with the surgical fastener and for fixing the fastener in position on the holder, and a surgical fastener engaged by said holder.

The above and other objects of the invention are also achieved by a surgical anchor for securement into an organic medium comprising, a first generally hollow cylindrical member having a plurality of longitudinally extending engaging fingers; a second generally hollow cylindrical member having a plurality of longitudinally extending engaging fingers, the fingers of said first member and said second member opposing each other and being interdigitated, there being provided cam surfaces on each member for engaging with fingers of the opposed member; a central longitudinally extending shaft disposed concentrically in said first and second members, the shaft having an abutment at a distal end abutting against the first of said members and having an engaging surface at a proximal end for engagement by an emplacement tool for emplacing the anchor into the organic medium; the members moving longitudinally relatively towards each other during emplacement of the anchor, the longitudinally extending fingers of each member abutting against the cam surface of the opposed member thereby causing the longitudinally extending fingers to move radially outwardly as the two members move relatively towards each other, the fingers of each member thereby penetrating into the organic medium to secure the anchor in position in the organic medium; and further wherein, the fingers of one member are of a different length than the fingers of the other opposed member, thereby causing the fingers of the one member having a longer length to begin engaging in the organic medium prior to the fingers of the other member.

The above and other objects of the invention are also achieved by a surgical anchor for securement into an organic medium comprising, a first generally hollow cylindrical member having a plurality of longitudinally extending engaging fingers; a second generally hollow cylindrical member having a plurality of longitudinally extending engaging fingers, the fingers of said first member and said second member opposing each other and being interdigitated, there being provided cam surfaces on each member for engaging with fingers of the opposed member; a central longitudinally extending shaft disposed concentrically in said first and second members, the shaft having an abutment at a distal end abutting against the first of said members and having an engaging surface at a proximal end for engagement by an emplacement tool for emplacing the anchor into the organic medium; the members moving longitudinally relatively towards each other during emplacement of the anchor, the longitudinally extending fingers of each member abutting against the cam surface of the opposed member thereby causing the longitudinally extending fingers to move radially outwardly as the two members move relatively towards each other, the fingers of each member thereby penetrating into the organic medium to secure the anchor in position in the organic medium; and further wherein a proximal most one of said member is crimped around said central longitudinally extending shaft thereby to secure said proximal most member frictionally to said shaft.

The above and other objects of the invention are also achieved by a surgical anchor for securement into organic medium comprising, a first generally hollow cylindrical member having a plurality of longitudinally extending engaging fingers; a second generally hollow cylindrical member having a plurality of longitudinally extending engaging fingers, the fingers of said first member and said second member opposing each other and being interdigitated, there being provided cam surfaces on each member for engaging with fingers of the opposed member; a central longitudinally extending shaft disposed concentrically in said first and second members, the shaft having an abutment at a distal end abutting against the first of said members and having an engaging surface at a proximal end for engagement by an emplacement tool for emplacing the anchor into the organic medium; the members moving longitudinally relatively towards each other during emplacement of the anchor, the longitudinally extending fingers of each member abutting against the cam surface of the opposed member thereby causing the longitudinally extending fingers to move radially outwardly as the two members move relatively towards each other, the fingers of each member thereby penetrating into the organic medium to secure the anchor in position in the organic medium; and further wherein said control longitudinally extending shaft includes a distal pointed end to enable self tapping of said suture anchor into said organic medium.

The above and other objects of the invention are also achieved by a surgical anchor comprising: a generally hollow cylindrical member having a plurality of longitudinally extending fingers, the fingers being adapted for radial movement so as to penetrate into an organic medium in which the suture anchor is emplaced; a longitudinally extending shaft extending through said member, the longitudinally extending shaft having a distal end of enlarged diameter to secure the member against axial movement, and further comprising a body surrounding said longitudinally extending shaft proximally of said member, said body having a cam surface for abutting against said longitudinally extending fingers of said member, said longitudinally extending shaft having an engaging surface at a proximal end for engagement by an emplacement tool, the surgical anchor being adapted to be engaged by said emplacement tool so that an axial force generated by said engagement tool will move said member axially against said cam surfaces, thereby causing said longitudinally directed fingers to move radially outwardly into engagement with an organic medium; the longitudinally extending shaft having a releasable connection, the releasable connection being located at a position distal to a proximal most end of said longitudinally extending fingers, so that when said anchor is emplaced in an organic medium, the proximal most end of said fingers are elevated above the proximal most end of said longitudinally extending shaft fixed in said organic medium.

The above and other objects of the invention are also achieved by a method for marking the location of a bore hole in an organic medium at a surgical site comprising: forming a hole in the organic medium; emplacing a surgical anchor in said hole in the medium having a proximally extending shaft, the shaft extending above the surface of the organic medium having the hole therein thereby to mark the location of the hole; the surgical anchor being of the type which can be emplaced into the hole in the organic medium without being fixed in the organic medium for later fixing in the organic medium.

The above and other objects of the invention are achieved by a surgical anchor for securement into an organic medium comprising, a first generally hollow cylindrical member having a plurality of longitudinally extending engaging fingers; a second generally hollow cylindrical member having a plurality of longitudinally extending engaging fingers, the fingers of said first member and said second member opposing each other and being interdigitated, there being provided cam surfaces on each member for engaging with fingers of the opposed member; a central longitudinally extending shaft disposed concentrically in said first and second members, the shaft having an abutment at a distal end abutting against the first of said members and having an engaging surface at a proximal end for engagement by an emplacement tool for emplacing the anchor into the organic medium; the members moving longitudinally relatively towards each other during emplacement of the anchor, the longitudinally extending fingers of each member abutting against the cam surface of the opposed member thereby causing the longitudinally extending fingers to move radially outwardly as the two members move relatively towards each other, the fingers of each member thereby penetrating into the organic medium to secure the anchor in position in the organic medium; and further wherein the fingers of one member are adapted to begin engaging in the organic medium prior to the fingers of the other member, thereby to assist in penetration of said fingers in the medium.

Other objects, features and advantages of the present invention will become apparent from the detailed description which follows.

BRIEF DESCRIPTION OF THE DRAWINGS

The invention will now be described in greater detail in the following detailed description with reference to the drawings in which.

DETAILED DESCRIPTION OF EMBODIMENTS OF THE INVENTION

With reference now to the drawings, a cartridge for a surgical bone anchor is generally identified with reference numeral 10. The suture anchor that the cartridge 10 is adapted to hold is indicated generally by reference numeral 40.

Figure 1:
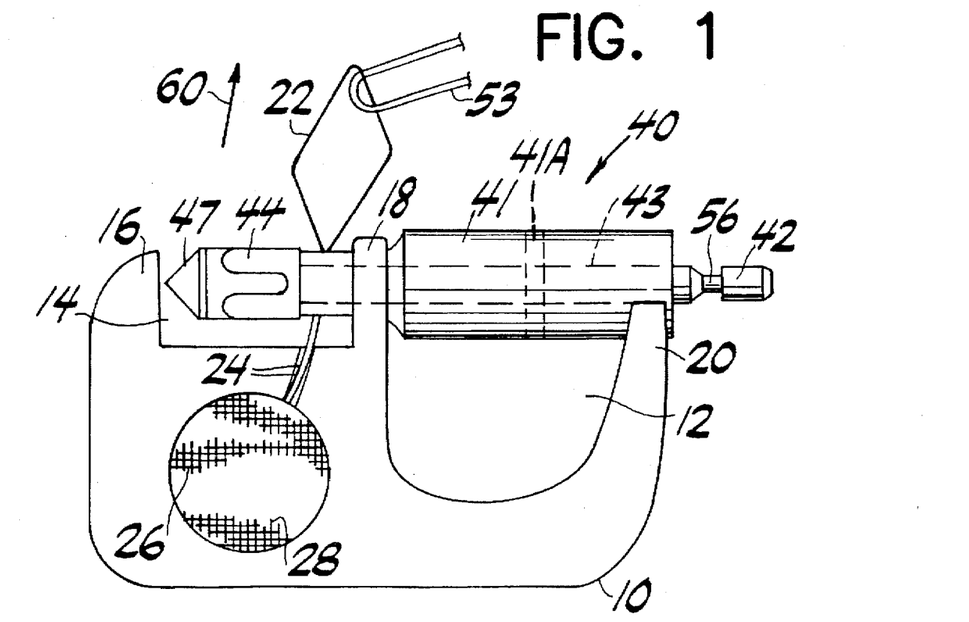
FIG. 1 shows a plan view of the cartridge and suture anchor according to the present invention prior to threading of a suture into the suture anchor.

In the embodiment illustrated, the cartridge 10 comprises a generally E-shaped member having two recesses 12 and 14 and three extending prongs 16, 18 and 20. Prong 18 is cup-shaped in a direction transverse to the longitudinal direction of the cartridge 10, as shown most clearly in FIG. 2. The cup-shaped recess is identified at 18A. Similarly, prong 20 is also cup-shaped, the cup-shaped recess identified as 20A. Prongs 18 and 20 are adapted to hold the suture anchor 40. In particular, the cup-shaped portion of prong 18 is adapted to hold the suture anchor 40 such that the suture anchor 40 snaps into the cup-shaped portion 18A of the prong 18 yet is easily removable.

Figure 6:
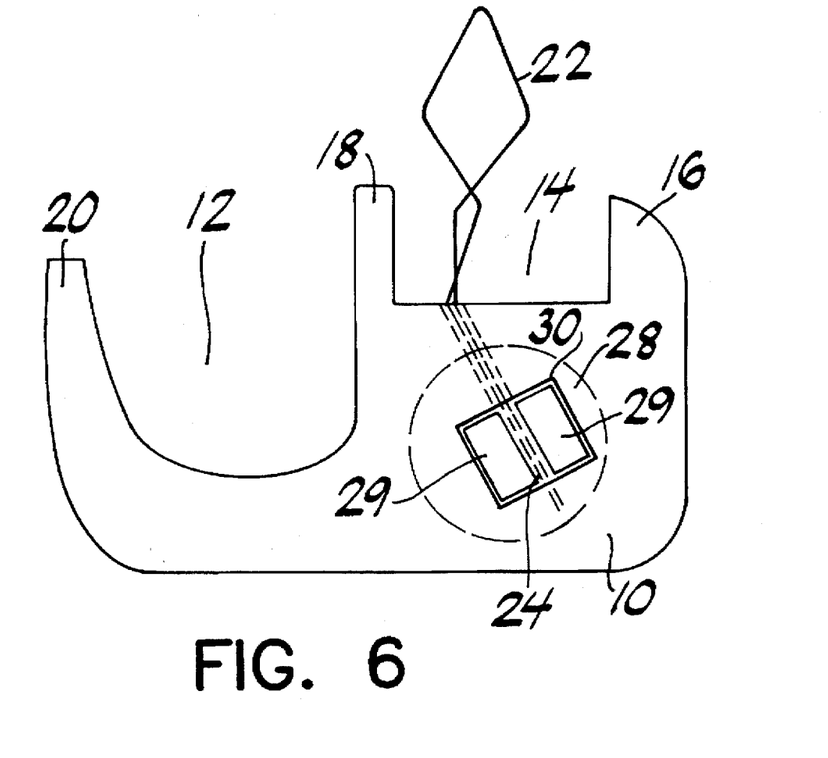
FIG. 6 shows a back view of the cartridge of FIGS. 1 and 2.

The cartridge 10 also includes a threading device 22 which comprises a looped spring wire 22. The looped wire 22 has two ends 24 which are secured in a region 26 of the cartridge 10 which comprises a recess into which a grooved finger gripping portion 28 is disposed. Finger gripping portion 28 comprises a disc having a suitable grooved or hatched pattern on an external surface and suitable snaps on a backside thereof for snapping into the cartridge body 10. At the same time, the ends 24 of the spring clip 22 are fastened by the disc member 28 to the cartridge 10. FIG. 6 shows the reverse side of the cartridge 10 showing the two wires 24 in phantom clamped in the circular recess in which the disc member 28 snaps. The disc member 28 has two rearwardly extending fingers 29 which facilitate snapping in of the disc member 28 in an opening 30 in the cartridge 10.

Figure 2:
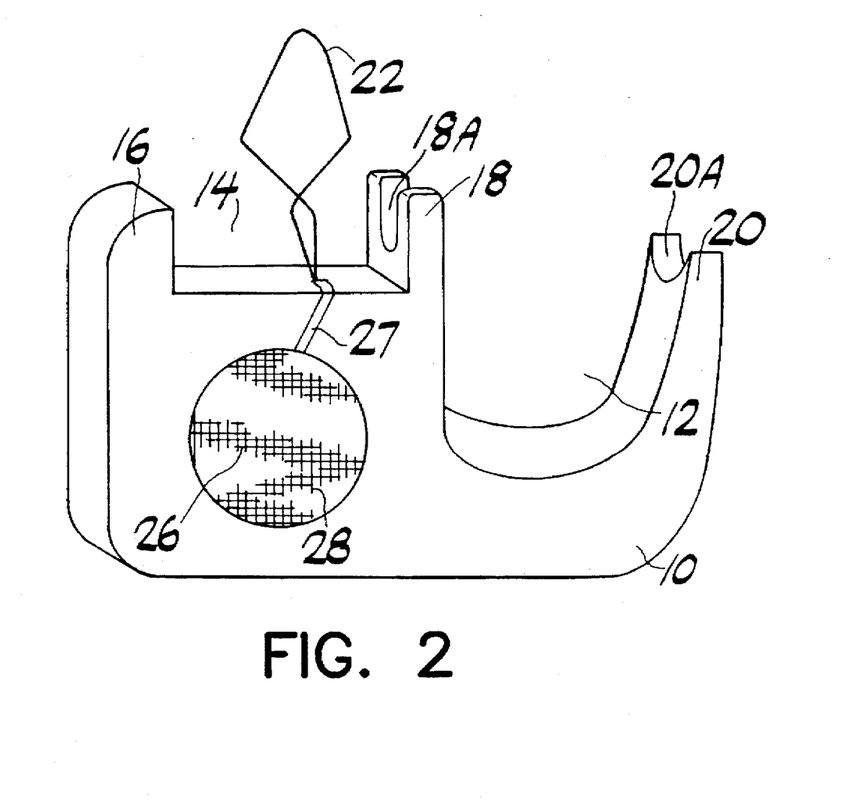
FIG. 2 shows a perspective view of the cartridge according to the present invention with the suture anchor removed.

As shown in FIGS. 1 and 2, the ends 24 of the spring wire threading member 22 are fed through a groove 27 disposed in the cartridge body 10 to the clamping site beneath disc member 28.

Figure 5:
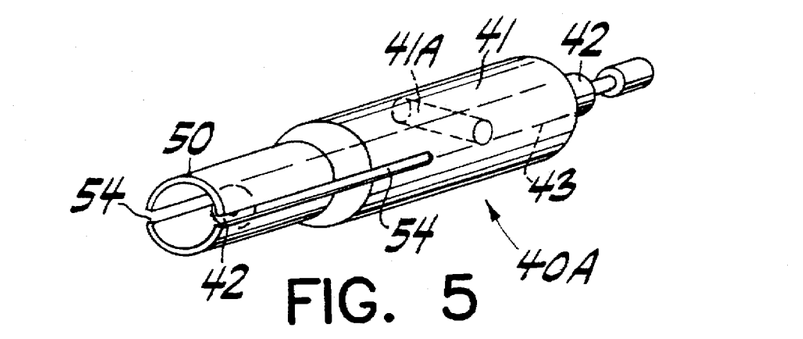
FIG. 5 shows a perspective view of a portion of the suture anchor which separates from the portion which is embedded in the medium, shown in FIG. 4, and which is discarded.

The surgical anchor 40 of the type disclosed herein is described in the above co-pending applications. The surgical anchor 40 comprises a substantially cylindrical main body portion 41, also shown in perspective view in FIG. 5. A rod 42 is slidably received in a longitudinal bore 43 in body 41. The rod 42 has an elongated slot 42A therein through which an alignment pin 41A extends. The alignment pin 41A is securely fitted in an aperture extending transversely through body 41. The alignment pin secures the rod 42 in body 41 for slidable movement limited by the length of slot 42A. The alignment pin thus keeps pieces 41 and 42 together, preventing their separation. Further, as will be explained below, after actuation of the anchor in a bore in a medium such as bone, the alignment pin keeps the disposable portion of rod 42 together with the body 41. As will be explained below, the body 41 and a portion of the rod 42 which breaks off from the distal end of the rod 42 upon activation form a disposable assembly.

Additionally, the alignment pin 41A helps to keep a suture slot 52 in rod 42 through which the suture is threaded in alignment with a slot 54 in the body 41, as described below. Thus, alignment pin 41A keeps the rod 42 from rotating with respect to the body 41.

The rod 42 is coupled slidably to a distal portion 44 of the surgical anchor 40 which is received in a bore in a medium in which it is to be implanted, i.e., into a bore in bone. The portion 44 comprises a rod portion 45 which is a continuation of and integral with the rod 42, being connected to the rod 42 via a frangible or breakable connection 46. The member 45 has a cone shaped or flared end 47 which secures two hollow cylindrical elements 48 and 49 having interdigitated fingers 48A and 49A and disposed around rod 45. The member 49 is secured against an abutment 50 which is a part of the cylindrical member 41. The portion 45 includes an aperture comprising a suture slot 52 therein through which the suture 53 is threaded.

In addition, the cylindrical main body portion 41 includes elongated slot 54 therein on each side thereof for rearward (proximal) disposition of the suture therein. The suture is looped through an aperture 52 in rod portion 45, as described below and the two ends of the suture are received in the grooves 54 when the suture anchor is being emplaced in the medium. The groove 54 continues into the portion 45 of the suture anchor portion which is embedded in the medium.

At the proximal end, the rod 42 includes a notch 56 which is engageable by an emplacement tool, described, for example, in applicant's above recited copending application.

The cartridge of the invention is preferably provided as a sterile packaged unit including cartridge body 10 and the surgical fastener 40 mounted thereon as shown in FIG. 1. The package can also include suture 53 threaded through loop 22. The combination of the cartridge 10 and fastener 40 and preferably suture 53 are contained within a sealed, sterile package, e.g., a clear plastic package, not shown.

Additionally, one or a plurality of the cartridges and surgical fasteners can be provided as a sterile packaged unit together with an emplacement tool, not shown, but described in the above co-pending application.

The spring threading member 22 is provided disposed through the opening 52 in rod 45 of the member 40.

Figure 7:
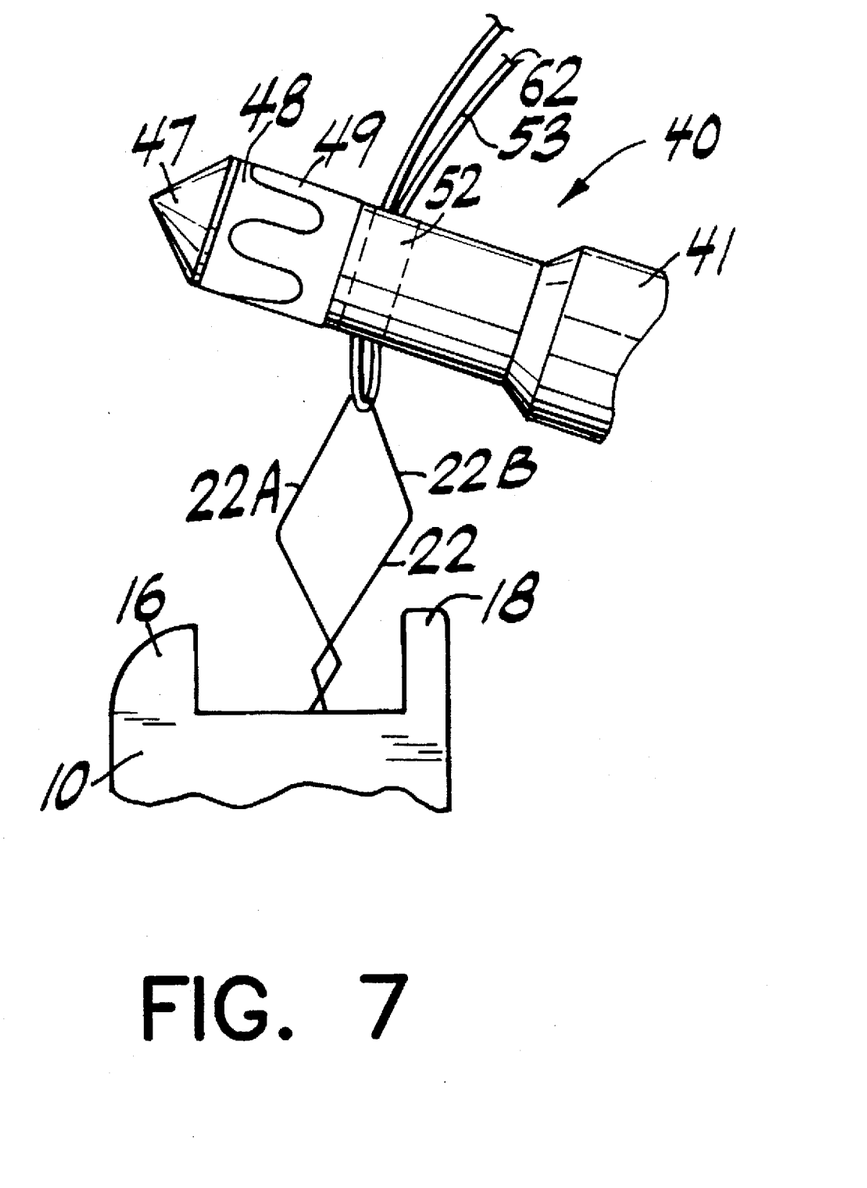
FIG. 7 shows the suture anchor after threading.
Figure 8:
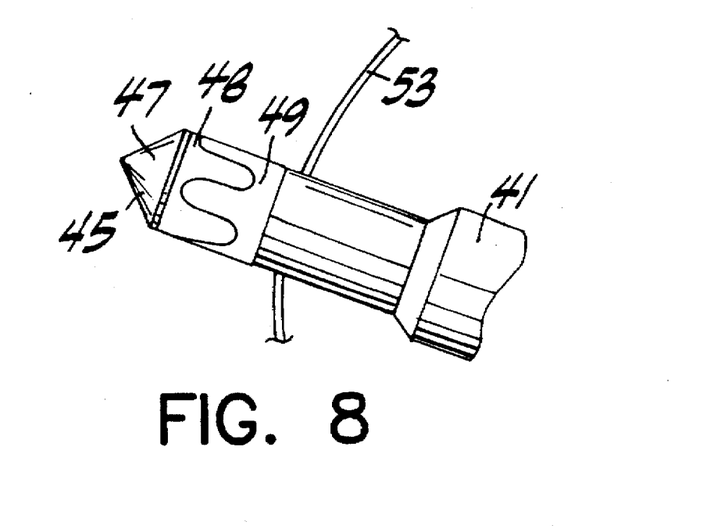
FIG. 8 shows the suture anchor fully threaded prior to emplacement in a medium such as bone.

To use the anchor, if not already threaded, a surgeon first threads the suture 53 through the loop 22, such that the suture 53 has a short end and a long end. The portion 26 provides a convenient place for grasping the cartridge body 10 with the fingers. The suture anchor 40 can now be removed from the cartridge 10 by relatively moving the suture anchor 40 with respect to the cartridge to separate the anchor and cartridge, e.g., by moving the anchor in the direction of arrow 60, thereby pulling the anchor 40 away from the cartridge 10. In so doing this, a loop of the suture 53 will be threaded through the bore 52 in the rod 45. This is shown in FIG. 7. The anchor 40 is pulled relatively away from the cartridge 10, with the result that free short end 62 of suture 53 will be pulled entirely through the bore 52 in rod 45, resulting in the position of the suture shown in FIG. 8. The two ends of the suture can then be guided along the slots 54 proximally. The cartridge body with the suture anchor 40 can then be engaged by the emplacement tool, not shown, which engages with the notch 56 in the rod 42.

The emplacement tool with the anchor 40 attached is then used to implant the anchor in a bore 69 in, e.g., bone 70, at the surgical site. See FIG. 4.

Figure 3:
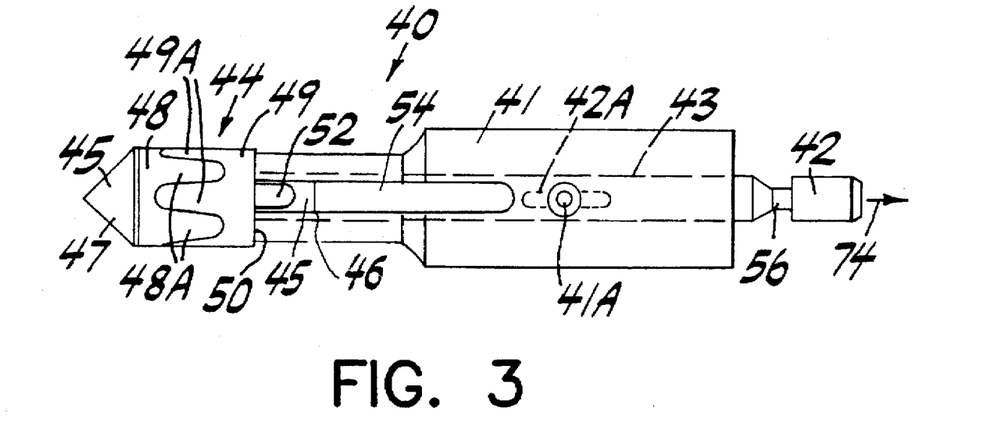
FIG. 3 is a top plan view of a suture anchor according to the above prior co-pending application removed from the cartridge.
Figure 4:
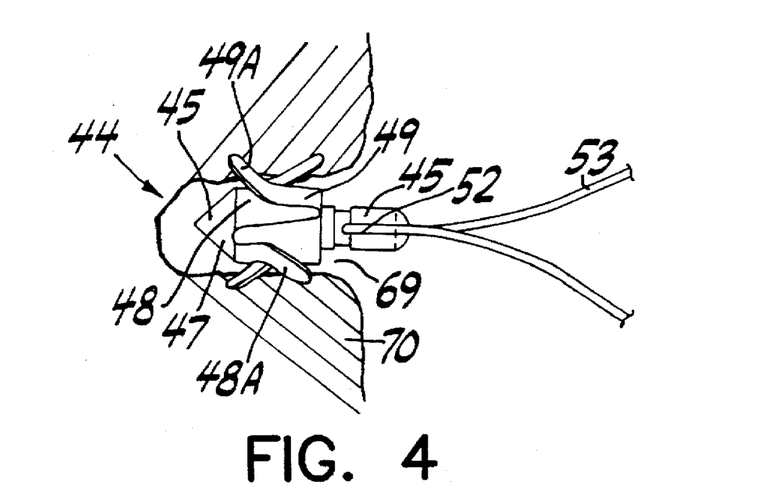
FIG. 4 shows the suture anchor after it has been embedded in a bore in a medium such as bone.

The emplacement tool is not shown, but is described and shown in Applicant's above co-pending application. When the tool is then actuated, rod 42 is moved slidably proximally, causing the portion 45 connected to the rod 42 also to move proximally. This causes elements 48 and 49, to move relatively toward each other, causing the fingers 48A and 49A to be displaced radially outwardly as they bear on respective cam surfaces of the other of the elements 48 and 49, as shown in FIG. 4, resulting in the fingers penetrating into the sidewalls of the bore 69 disposed in the medium 70, such as bone. The fingers penetrate into the bone 70 thereby locking the anchor into the bore in the bone. After the fingers 48A and 49A are caused to lock the anchor into the medium, the emplacement tool is further actuated. The force acting in the direction of arrow 74, see FIG. 3, causes the frangible connection 46 between rod portion 42 and rod portion 45 to snap, resulting in separation of the embedded surgical anchor portion 44 from the rod portion 42 and thus cylindrical member 41. The portion 40A comprising the cylindrical member 41 and the rod 42, as shown separately in FIG. 5 in perspective view, can then be discarded.

Preferably, anchor 40, including all parts thereof (41, 42, 45, 48 and 49 and all subparts), is made of a suitable biocompatible material, such as a stainless steel, titanium, etc. as known to those of skill in the art.

The frangible connection 46 may be made by disposing a groove in the rod 42 which weakens the rod 42 so that it snaps at a prescribed amount of tensile force in rod 42.

When anchor 40 is removed from the cartridge 10, the two opposed portions 22A and 22B of the wire forming the loop of the threading member 22 will move toward each other, squeezing to conform to the size of the aperture 52. After the suture wire loop 22 passes completely through the aperture 52, the loop will spring back into the shape shown in the drawing figures.

Figure 9:
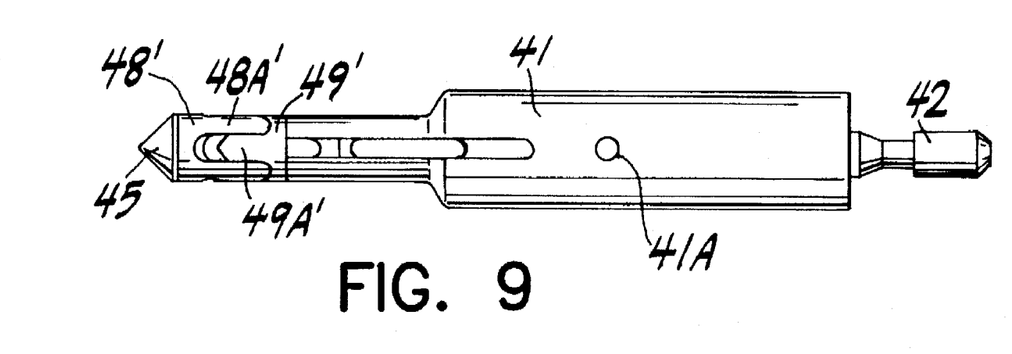
FIG. 9 is a plan view of a modified form of the suture anchor shown in FIG. 1.
Figure 10:
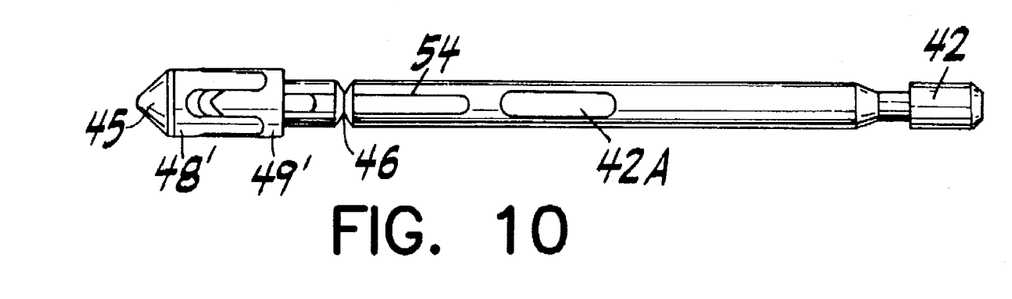
FIG. 10 is a plan view of a portion of the suture anchor of FIG. 9.
Figure 14:
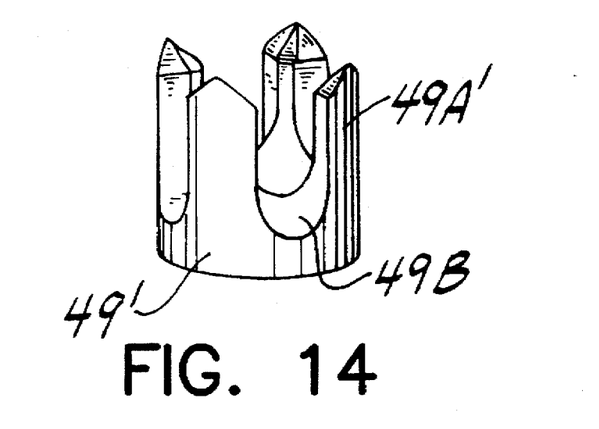
FIG. 14 shows one of the hollow cylindrical engaging elements of the anchor of FIG. 9.
Figure 15:
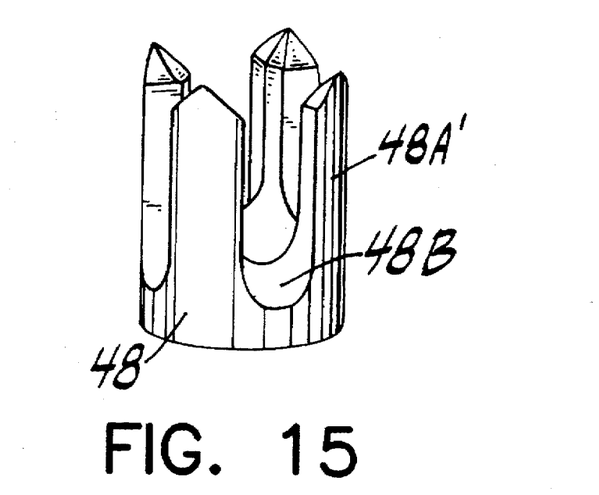
FIG. 15 shows the other of the hollow cylindrical engaging elements of FIG. 9.

FIG. 9 shows a modified form of the suture anchor of FIG. 1. Like components are indicated by like reference numerals. A major distinction between the suture anchor of FIG. 9 and that of FIG. 1 is that the members 48' and 49' have fingers 48A' and 49A' of different lengths, as shown more particularly in FIGS. 11, 14 and 15. FIGS. 14 and 15 show perspective views of the elements 48' and 49'. The reason for making the elements 48' and 49' have different length engaging fingers 48A' and 49A' is so that a staged deployment of the suture anchor can be achieved. It has been determined, in some instances, particularly in very hard cortical bone, that it is sometimes difficult to achieve full deployment of all fingers of the elements 48 and 49 of the anchor of FIG. 1. The reason for this is that all fingers deploy at approximately the same time. It has been found that if a staged deployment is used, i.e., allowing the fingers of one element 48 or 49 to deploy first, and then later have the fingers of the other of the elements 48 and 49 deploy later, that a more secure fastening of the suture anchor can be achieved.

To this end, the suture anchor of FIG. 9 has an engaging element 48' having longer fingers 48A' than the fingers 49A' of the element 49'. In this way, the fingers 48A' engage first by moving against cam surfaces 49B of the member 49' having the shorter fingers 49A'. Once the fingers 48A' of the element 48 have engaged to some extent in the bone, and thus moved radially and longitudinally, the fingers 49A' of the member 49' will then come into abutment with the cam surfaces 48B of the member 48. The fingers 49A' will begin to penetrate into the bone while the fingers 48A' continue the penetration previously started. As some point, once full penetration has been achieved, the frangible connection 46 will break, leaving the member 48', 49' and 45 secured in the bone. The staged deployment provided by this embodiment allows a greater force to be applied initially to a smaller number of fingers (fingers 48A') because the penetrating force is applied initially only to the fingers of element 48'. This allows fingers 48A' to penetrate with greater force into the bone.

Figure 11:
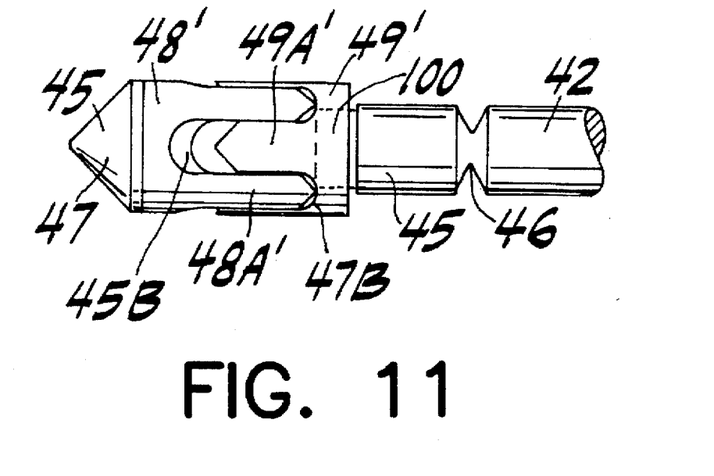
FIG. 11 shows a detail of FIG. 10.

As shown in FIG. 11, in order to secure rod 45 from moving distally into the bore, (it cannot move proximally because of the flare of the portion 47), a portion of the member 49', in the area shown shaded indicated at 100 in FIG. 11, is provided with a crimp so that generally cylindrical member 49' has a somewhat flattened oval shape in cross-section, frictionally engaging the rod 45.

Figure 11A:
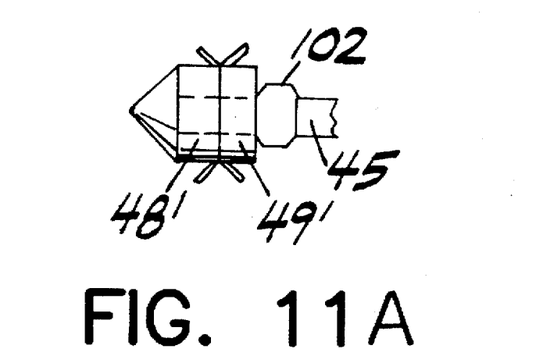
FIG. 11A shows a modified form of the anchor of FIG. 9.
Figure 12:
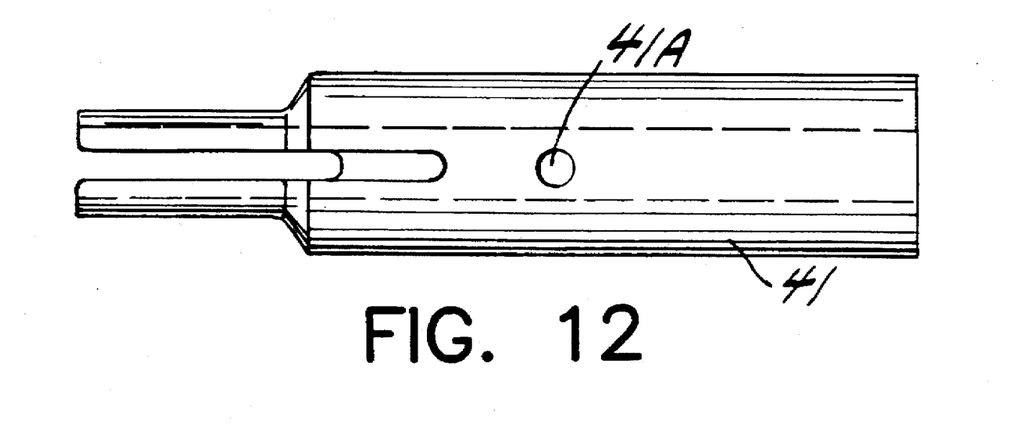
FIG. 12 shows a detail of a portion of the anchor of FIG. 9.
Figure 13:
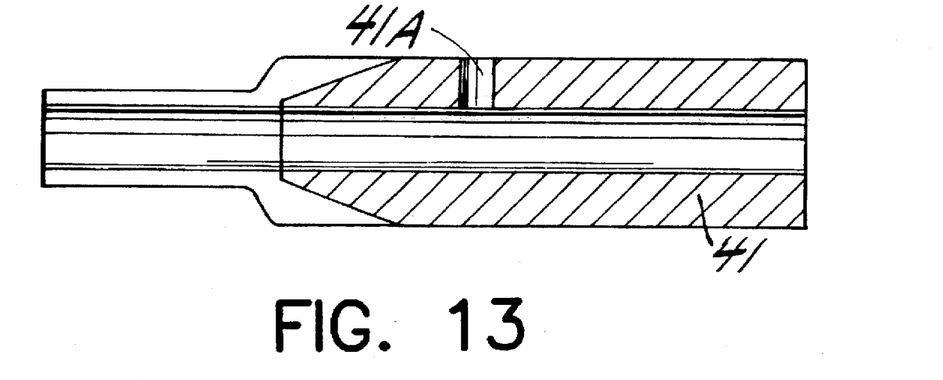
FIG. 13 shows a further detail of a portion of the anchor of FIG. 9, partly in cross-section.

As an alternative, as shown in FIG. 11a, rod 45 may also be provided with an enlarged diameter portion 102 with the member 49' being crimped so that upon actuation of the anchor, the member 49 jumps over the enlarged portion 102 of shaft 45 to secure the shaft 45 in position against any axial movement.

Figure 16:
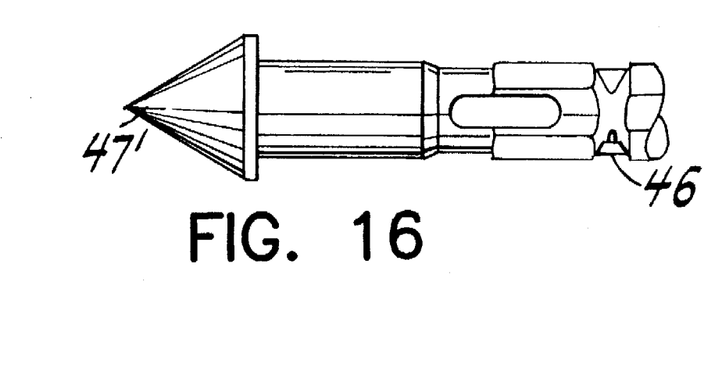
FIG. 16 shows yet another modified form of the suture anchor.

FIG. 16 shows a further embodiment of a portion of the suture anchor according to the present invention. Again, like reference numerals are used for like components. The major difference between the embodiment shows in FIG. 16 and the other embodiments is that tip 47' is made with a sharp point. In this embodiment, the anchor can be tapped into the bone without requiring a bore hole to be drilled. This embodiment of the suture anchor thus forms self-tapping and forms its own borehole. In order to assist tapping in of the suture anchor, the emplacement tool, to which the suture anchor is attached prior to insertion, is provided with a tapping surface on a proximal end. The tapping surface can be struck with a suitable instrument such as a hammer.

Figure 17:
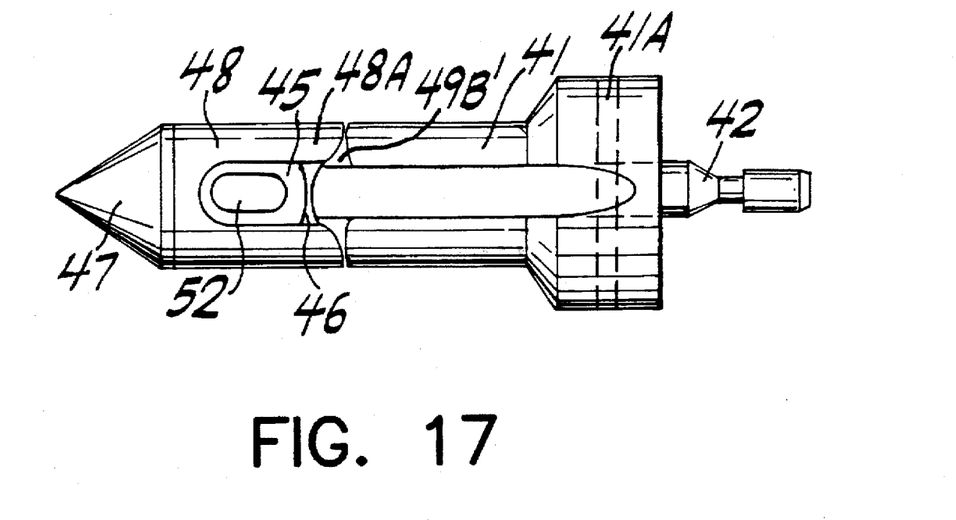
FIG. 17 shows yet another embodiment of the suture anchor, one having a low profile.
Figure 18:
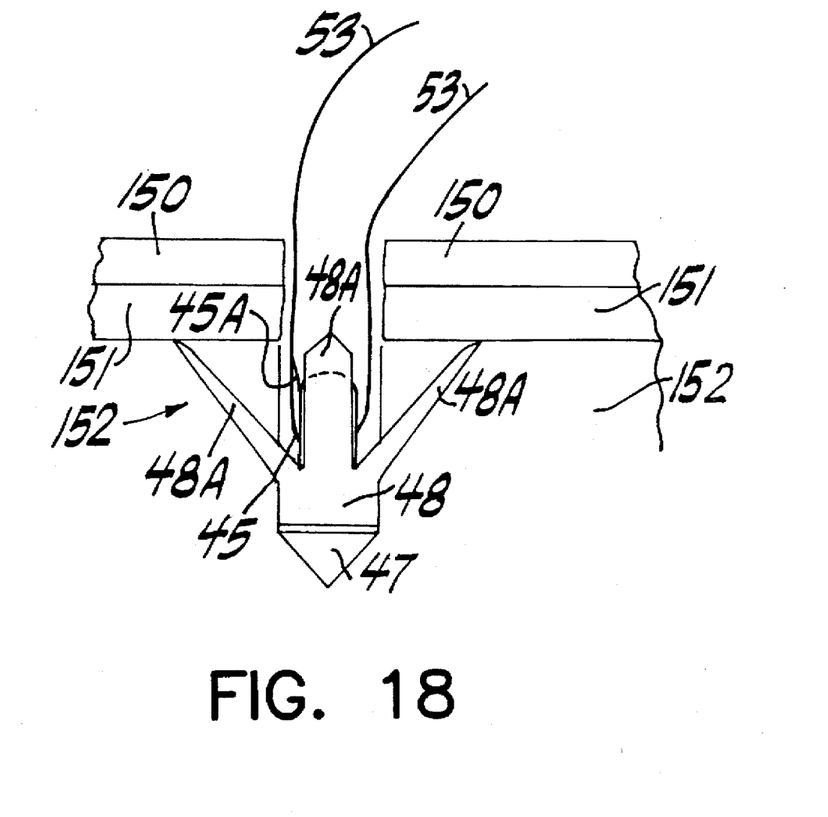
FIG. 18 shows how the anchor of the present invention can be used in soft cancellous bone.

FIG. 17 shows yet another embodiment of the suture anchor according to the present invention. In this embodiment, the suture anchor is formed such that the frangible connection 46 is disposed so that after the fingers 48 engage into the bore, the proximal end of the penetrating fingers are at a level no lower than the proximal tip of the rod 45 to which the suture is affixed. In this way, it is assured that no portion of the suture anchor can stand above the top surface of the bone. FIG. 18 shows the suture anchor of FIG. 17 emplaced in a bore in bone, showing how the proximal end 45A of the rod 45 is below the proximal end of the penetrating fingers 48A. As also shown in FIGS. 17 and 18, the suture anchor only includes a single cylindrical engaging member 48, the fingers 48A not being interdigitated with another cylindrical engaging element as in the previous embodiments. In this embodiment, the body 41 is provided with suitable cam surfaces 49B' for causing a radial extension of the fingers 48A. Also shown in FIG. 16, this embodiment includes a sharp three pointed distal end 47 so that it is also self tapping, if desired to be used in this way.

As shown in FIG. 18, the anchor of the present invention operates much like a grappling hook, particularly when it is deployed in soft cancellous bone. As shown in FIG. 18, the cortical or hard layer of the bone is indicated at 150. The less hard subcortical layer is shown at 151. The soft cancellous layer is indicated at 152. When the anchor is deployed, the fingers 48A extend into the soft cancellous bone. As pressure is exerted on the sutures 53, which tend to pull the anchor out of the bore hole, the fingers may move axially up against the bottom surface of the harder subcortical bone 151, thereby securely holding the fastener in position.

The anchor of the present invention provides a number of advantages over suture anchors and prosthetic anchors of the prior art. One advantage is that the anchor causes no damage to tissue upon insertion, because the anchor, in the case of a predrilled bore, does not require excessive force to be inserted. This results in less damage generally to tissue, since the anchor is not a force fit" and no external force need be applied to the tissue in order to insert the anchor. Once the anchor is inserted, it is activated by an emplacement tool which causes the fingers 48A, 49A to penetrate into the bone.

Another advantage of the anchor according to the present invention is that the anchor can be emplaced and removed prior to activation. For example, upon initial emplacement of the anchor but prior to activation of the fingers 48A, 49A to penetrate into the bone, if the surgeon believes that the anchor is improperly located, the anchor can be easily removed, a new hole drilled and the anchor emplaced at the appropriate point.

Another advantage of the anchor according to the present invention is that it can be made very small and yet is adequately strong as a suture or prosthetic anchor.

A further advantage of the anchor according to the present invention is that relatively low forces are necessary to emplace the anchor. The emplacement tool as described in the above co-pending patent application magnifies the force exerted by the surgeon many times to activate the anchor. Accordingly, the anchor can be emplaced into very hard bone, requiring a relatively low finger force to be exerted by the surgeon which is magnified into a larger force to achieve penetration into the bone. In this respect, the finger force required by the surgeon to activate the anchor is essentially independent of the type of bone and bone quality.

A further aspect of the present invention is that the anchor can be inserted into a bore hole in bone and prior to actuation, can be used as a convenient marker for the location of the bore hole. During surgery, body fluids will tend to cover over bore holes drilled in tissue, making them difficult to locate after an amount of time has passed by. According to the present invention, the anchor can be inserted into the hole immediately after it is drilled and not activated to allow marking of the location of the hole. Once the surgeon is satisfied with the emplacement of the anchor or anchors, they can then be actuated by engaging the anchors with the emplacement tool.

A further aspect of the present invention is that upon insertion no wall damage by threads or spring fingers is caused to the bore, as in prior art surgical anchors.

In the embodiment shown in FIG. 17 employing a self-tapping anchor having a sharp pointed end 47, it is noted that even though the anchor is tapped into the bone and is self-tapping, until the anchor itself is activated by causing the fingers 48A to move radially into the bone tissue, the anchor can be fully retracted at any time prior to activation.

The present invention can also be used as a bone plug, e.g., to plug a lower portion of a bore hole in bone to prevent, e.g., cement from extruding past the bone plug. For example, as shown in FIG. 18, if the surgical anchor is inserted into a bore hole, it can be used to seal off portions of the bore hole below the surgical anchor. In this way, cement deposited in the bore hole above the anchor is prevented from extruding into the lower portions of the bore hole.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. A cartridge for holding a surgical fastener in position for ease of handling, comprising:
    a holder having a surface for grasping by a user, the holder having a concave surface for engagement with the surgical fastener and for fixing the fastener in position on the holder; and
    a threading loop extending from the holder for extending through an aperture in the surgical fastener.

2. The cartridge of claim 1, wherein the holder comprises a member having two projecting portions, each of which has a concave surface for engaging the fastener.

3. The cartridge of claim 2 wherein the surgical fastener is generally cylindrical and each concave surface is cup-shaped.

4. The cartridge of claim 1, wherein the holder comprises a generally E-shaped member having three projecting portions, two of said projecting portions having a concave surface for engaging the fastener, two recesses being formed between the projections, the threading loop extending from one of said recesses.

5. The cartridge of claim 1, further comprising a surgical fastener engaged by said holder with the threading loop disposed through said aperture in the surgical fastener.

6. The cartridge of claim 5, wherein the surgical fastener comprises a cylindrical member, a rod disposed through the cylindrical member, the rod having a flared end, an engaging member adjacent the flared end for engagement with side-walls of a bore in a bio-organic medium, the rod being disposed through the engaging member, the engaging member being disposed between the flared end of the rod and the cylindrical member, the rod further having an end extending from an opposite end of the cylindrical member for engagement by an emplacement tool for the surgical fastener, a frangible connection being disposed in the rod such that once a predetermined amount of tensile force has been applied by the emplacement tool, the frangible connection breaks, separating the engaging member from the cylindrical member with a portion of the rod disposed in the engaging member and another portion disposed in the cylindrical member.

7. The cartridge of claim 6, wherein the engaging member includes a plurality of longitudinally extending fingers for radial outward extension into a bore in a medium upon actuation by an emplacement tool.

8. The cartridge of claim 6, further wherein the rod has an aperture for receiving a suture, the aperture disposed distally of said frangible connection so that the aperture is in the portion of the rod disposed in the engaging member.

9. The cartridge of claim 8, further comprising a suture disposed through said threading loop.

10. The cartridge of claim 6, wherein the frangible connection comprises a weakened portion of the rod.

11. The cartridge of claim 10, wherein the frangible connection comprises a groove formed circumferentially in the rod to weaken the rod so that the rod breaks at a predetermined tensile force in the rod.

12. The cartridge of claim 1, wherein the threading loop comprises a loop of spring wire.

13. A combination comprising:
    a cartridge for holding a surgical fastener in position for ease of handling, the cartridge comprising:
        a holder having a surface for grasping by a user, the holder having a surface for engagement with the surgical fastener and for fixing the fastener in position on the holder;
        a threading loop extending from the holder for extending through an aperture in the surgical fastener; and
        a surgical fastener engaged by said holder with the threading loop disposed through the aperture in the surgical fastener.

14. The combination of claim 13, further comprising a sterile package in which the holder and surgical fastener are provided.

15. The combination of claim 14, further comprising a suture provided in said package.

16. The combination of claim 15, wherein the suture is threaded through the threading loop.

17. The combination of claim 13, wherein the holder comprises a member having two projecting portions, each of which has a concave surface for engaging the fastener.

18. The combination of claim 13, wherein the holder comprises a generally E-shaped member having three projecting portions, two of said projecting portions having a concave surface for engaging the fastener, two recesses being formed between the projections, the threading loop extending from one of said recesses.

19. The combination of claim 13, wherein the surgical fastener comprises a cylindrical member, a rod disposed through the cylindrical member, the rod having a flared end, an engaging member adjacent the flared end for engagement with sidewalls of a bore in a bio-organic medium, the rod being disposed through the engaging member, the engaging member being disposed between the flared end of the rod and the cylindrical member, the rod further having an end extending from an opposite end of the cylindrical member for engagement by an emplacement tool for the surgical fastener, a frangible connection being disposed in the rod such that once a predetermined amount of tensile force has been applied by the emplacement tool, the frangible connection breaks, separating the engaging member from the cylindrical member with a portion of the rod disposed in the engaging member and another portion disposed in the cylindrical member.

20. The combination of claim 19, further wherein the rod has an aperture for receiving a suture, the aperture disposed distally of said frangible connection so that the aperture is in the portion of the rod disposed in the engaging member.

21. The combination of claim 20, further comprising a suture disposed through said threading loop.

22. The combination of claim 13, wherein the threading loop comprises a loop of spring wire.

23. The combination of claim 19, wherein the frangible connection comprises a weakened portion of the rod.

24. The combination of claim 23, wherein the frangible connection comprises a groove formed circumferentially in the rod to weaken the rod so that the rod breaks at a predetermined tensile force in the rod.

25. A combination comprising:
- a cartridge for holding a surgical fastener in position for ease of handling, the cartridge comprising:
  - a holder having a surface for grasping by a user, the holder having a surface for engagement with the surgical fastener and for fixing the fastener in position on the holder; and
  - a surgical fastener engaged by said holder and further wherein the holder comprises a member having two projecting portions, each of which has a cup-shaped surface for engaging the fastener.

26. The combination of claim 25, further comprising:
- a threading loop extending from the holder for extending through an aperture in the surgical fastener;
- the threading loop being disposed through he aperture in the surgical fastener.

27. The combination of claim 26, further comprising a sterile package in which the holder and surgical fastener are provided.

28. The combination of claim 27, further comprising a suture provided in said package.

29. The combination of claim 28, wherein the suture is threaded through the threading loop.

30. The combination of claim 27, further comprising an emplacement tool for the surgical fastener in said package.

31. The combination of claim 26, wherein the holder comprises a generally E-shaped member having three projecting portions, two of said projecting portions having a cup-shaped surface for engaging the fastener, two recesses being formed between the projections, the threading loop extending from one of said recesses.

32. The combination of claim 26, further comprising a suture disposed through said threading loop.

33. The combination of claim 26, wherein the threading loop comprises a loop of spring wire.

34. The combination of claim 25 wherein the surgical fastener is generally cylindrical and the holder surface for engagement with the fastener is cup-shaped.

35. The combination of claim 25, wherein the surgical fastener comprises a cylindrical member, a rod disposed through the cylindrical member, the rod having a flared end, an engaging member adjacent the flared end for engagement with sidewalls of a bore in a bio-organic medium, the rod being disposed through the engaging member, the engaging member being disposed between the flared end of the rod and the cylindrical member, the rod further having an end extending from an opposite end of the cylindrical member for engagement by an emplacement tool for the surgical fastener, a frangible connection being disposed in the rod such that once a predetermined amount of tensile force has been applied by the emplacement tool, the frangible connection breaks, separating the engaging member from the cylindrical member with a portion of the rod disposed in the engaging member and another portion disposed in the cylindrical member.

36. The combination of claim 35, further wherein the rod has an aperture for receiving a suture, the aperture disposed distally of said frangible connection so that the aperture is in the portion of the rod disposed in the engaging member.

37. The combination of claim 35, wherein the frangible connection comprises a weakened portion of the rod.

38. The combination of claim 37, wherein the frangible connection comprises a groove formed circumferentially in the rod to weaken the rod so that the rod breaks at a predetermined tensile force in the rod.

39. The combination of claim 35, wherein the engaging member comprises two cylindrical elements disposed coaxially about said rod, each having longitudinally extending fingers interdigitated with each other, the fingers being movable radially outwardly for penetration into and engagement with a bore in a medium into which the engaging member is to be secured by a force exerted on said rod which causes the two cylindrical elements to move relatively toward each other.

* * * * *